United States Patent [19]

Desbois et al.

[11] 4,322,369

[45] Mar. 30, 1982

[54] PREPARATION OF ALKYL CYANOACETATES

[75] Inventors: Michel Desbois, Rillieux; Gerard Soula, Meyzieu, both of France

[73] Assignee: Rhone-Poulenc Industries, Paris, France

[21] Appl. No.: 216,363

[22] Filed: Dec. 15, 1980

[30] Foreign Application Priority Data

Dec. 20, 1979 [FR] France .................. 79 31221

[51] Int. Cl.$^3$ .......................... C07C 120/04
[52] U.S. Cl. .......................... 260/465.4
[58] Field of Search ................. 260/465.4

[56] References Cited

U.S. PATENT DOCUMENTS

| | | | |
|---|---|---|---|
| 2,928,877 | 3/1960 | Jaul et al. | 260/584 |
| 2,985,682 | 5/1961 | Raffelson | 260/464 |
| 3,360,540 | 12/1967 | Sennewald et al. | 260/465.4 X |
| 3,384,654 | 5/1968 | Sennewald et al. | 260/465.4 X |
| 3,773,808 | 11/1973 | Wesselman | 260/465.4 |
| 4,174,347 | 11/1979 | Bertola | 260/465.4 |

FOREIGN PATENT DOCUMENTS

| | | |
|---|---|---|
| 1302365 | 7/1962 | France . |
| 1383366 | 11/1964 | France . |
| 1447526 | 6/1966 | France . |
| 1450529 | 7/1966 | France . |
| 2021641 | 7/1970 | France . |
| 2357533 | 7/1977 | France . |

OTHER PUBLICATIONS

Hackh's Chemical Dictionary, 4th Ed., (1969), pp. 240, 605 and 650.

*Primary Examiner*—Joseph Paul Brust
*Attorney, Agent, or Firm*—Burns, Doane, Swecker & Mathis

[57] ABSTRACT

The alkyl cyanoacetates are prepared by reacting an alkyl chloracetate with an excess of an alkali metal cyanide, in an inert solvent and in the presence of at least one tertiary amine sequestering agent having the formula:

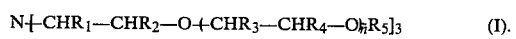

$$N{-}[CHR_1{-}CHR_2{-}O{-}(CHR_3{-}CHR_4{-}O)_n R_5]_3 \qquad (I).$$

21 Claims, No Drawings

PREPARATION OF ALKYL CYANOACETATES

BACKGROUND OF THE INVENTION

1. Field of the Invention

The present invention relates to the preparation of alkyl cyanoacetates, and, more especially, to the preparation of alkyl cyanoacetates by reacting the alkyl chloracetates with an alkali metal cyanide, notably sodium cyanide.

2. Description of the Prior Art

It is known to this art to prepare cyanoacetic esters by reacting an at least equimolar amount of a haloacetate with an alkali metal cyanide in an inert solvent, in the presence of hydrocyanic acid, at a temperature between 20° and 250° C. and under a pressure between 1 and 6 atmospheres. Compare French Pat. No. 1,447,526.

The hydrocyanic acid is not consumed during the reaction; rather, it serves to suppress any secondary reactions between the haloacetate and the already-formed cyano ester with attendant formation of by-products. According to this French Pat. No. 1,447,526 patent, it is particularly advantageous to use between 1.1 and 6 moles of haloacetate per mole of the alkali metal cyanide, and between 0.1 and 4 moles of HCN per mole of said alkali metal cyanide. The solvents suggested are principally alcohols corresponding to the alcohol moiety of the ester employed.

The principal disadvantage of this type of process is that, in order to utilize reaction velocities compatible with acceptable industrial production rates, it is necessary to conduct the reaction with solvent reflux. This poses severe safety problems, because under these conditions the toxic hydrocyanic acid is in the vapor phase.

It is also known to this art to prepare cyanoacetates by reacting sodium or potassium cyanide with a haloacetate; compare published French Patent Application No. 2,021,641. One characteristic of this process is the fact that the reaction is effected in acetonitrile using an excess of cyanide. According to the applicant, it is possible to conduct the reaction either in the presence or absence of water. It would also appear that the embodiment of conducting the process in the presence of water is industrially feasible only if the ester employed is derived from a tertiary alcohol; in fact, outside of these limits the hydrolysis of the ester function occurs to such extent as to be inconsistent with the economics of the process. But, if the reaction be carried out in the absence of water, it proceeds too slowly and the degree of conversion is quite poor.

Thus, serious need exists in this art for an improved process for cyanoacetate preparation that is not limited to one definite type of ester, that may be carried out at low temperatures under improved safety conditions, while at the same time permitting satisfactory reaction rates and degrees of conversion compatible with production on an industrial level.

See also U.S. Pat. No. 2,985,682; French Pat. Nos. 1,383,366, 1,447,526, 1,450,529, 2,021,641 and 2,357,533.

SUMMARY OF THE INVENTION

Accordingly, a major object of the present invention is the provision of such improved process for the preparation of alkyl cyanoacetates by reacting an alkyl chloracetate with at least one alkali metal cyanide, with an excess of cyanide ions, the process being characterized in that the reaction is carried out in an inert solvent in the presence of at least one sequestering agent having the structural formula:

$$N + CHR_1 - CHR_2 - O - (CHR_3 - CHR_4 - O)_n - R_5]_3 \quad (I)$$

wherein n is an integer greater than or equal to 0 and less than or equal to approximately 10 ($0 \leq n \leq 10$): $R_1$, $R_2$, $R_3$, $R_4$, which may be identical or different, represent a hydrogen atom or a lower alkyl radical having from 1 to 4 carbon atoms, $R_5$ represents an alkyl or cycloalkyl radical having from 1 to 12 carbon atoms, a phenyl radical or a radical of the formula

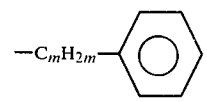

or

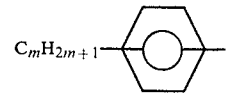

m having a value between 1 and approximately 12.

DETAILED DESCRIPTION OF THE INVENTION

More particularly according to the invention, salient characteristic thereof is that the sequestering agent having the Formula (I) forms a complex with the alkali metal cyanide, such complex being more soluble in the solvent utilized than is the alkali metal cyanide itself.

In a preferred embodiment of the invention, in the at least one sequestering agent having the Formula (I), $R_1$, $R_2$, $R_3$ and $R_4$ are preferably hydrogen or methyl, and $R_5$ and n are as above defined.

Even more preferably among such preferred sequestering agents, n is greater than or equal to 0 and less than or equal to 3, and $R_5$ is an alkyl radical having 1 to 4 carbon atoms.

Exemplary of such preferred sequestering agents are:

(1) Tris(3-oxaheptyl)amine having the formula:

$$N + CH_2 - CH_2 - O - C_4H_9)_3$$

(2) Tris(3,6-dioxaheptyl)amine having the formula:

$$N + CH_2 - CH_2 - O - CH_2 - CH_2 - O - CH_3)_3$$

(3) Tris(3,6,9-trioxadecyl)amine having the formula:

$$N + CH_2 - CH_2 - O - CH_2 - CH_2 - O - CH_2 - CH_2 - O - CH_3)_3$$

(4) Tris(3,6-dioxaoctyl)amine having the formula:

$$N + CH_2 - CH_2 - O - CH_2 - CH_2 - O - C_2H_5)_3$$

(5) Tris(3,6,9-trioxaundecyl)amine having the formula:

$$N + CH_2 - CH_2 - O - CH_2 - CH_2 - O - CH_2 - CH_2 - O - C_2H_5)_3$$

(6) Tris(3,6-dioxanonyl)amine having the formula:

$$-N\text{-}(CH_2-CH_2-O-CH_2-CH_2-O-C_3H_7)_3-$$

(7) Tris(3,6,9-trioxadodecyl)amine having the formula:

$$N\text{-}(CH_2-CH_2-O-CH_2-CH_2-O-CH_2-CH_2-O-C_3H_7)_3$$

(8) Tris(3,6-dioxadecyl)amine having the formula:

$$N\text{-}(CH_2-CH_2-O-CH_2-CH_2-O-C_4H_9)_3$$

(9) Tris(3,6,9-trioxatridecyl)amine having the formula:

$$N\text{-}(CH_2-CH_2-O-CH_2-CH_2-O-CH_2-CH_2-O-C_4H_9)_3$$

(10) Tris(3,6-dioxa-4-methylheptyl)amine having the formula:

$$N\text{-}(CH_2-CH_2-O-CHCH_3-CH_2-O-CH_3)_3$$

(11) Tris(3,6-dioxa-2,4-dimethylheptyl)amine having the formula:

$$N\text{-}(CH_2-CHCH_3-O-CHCH_3-CH_2-O-CH_3)_3.$$

The amino sequestering agents employed in the process according to the invention are per se known to the prior art. Thus, French Pat. No. 1,302,365 reports the preparation of the tertiary amines $N\text{-}(CH_2-CH_2-O-CH_3)_3$ and $N\text{-}(CH_2-CH_2-O-CH_2-CH_2-O-CH_3)_3$ as by-products of the synthesis of the corresponding primary and secondary amines, such primary and secondary amines being useful intermediates in the preparation of pharmaceuticals, corrosion inhibitors, intermediates in the preparation of agricultural chemicals and emulsifiers. It will be appreciated, though, that whatever the use suggested for any of the amines disclosed in the noted French Pat. No. 1,302,365 patent, including those tertiary amines useful in the present process, such use is completely alien to the field of this invention.

The solvent employed is preferably selected from among the group comprising alcohols and nitriles. As examples, the following are representative: methanol, ethanol, the propanols, the butanols, acetonitrile and propionitrile. Among these, acetonitrile is especially preferred.

According to a preferred embodiment of the invention, the subject reaction is carried out in the additional presence of hydrocyanic acid. The latter does not adversely affect the action of the sequestering agent, but reduces the formation of undesirable secondary products, or by-products.

The process according to the invention is applicable to the reaction of an alkyl chloracetate having the formula:

$$Cl-CH_2-COOR$$

wherein R is a lower alkyl radical having from 1 to about 5 carbon atoms.

The following chloracetates, however, are especially preferred in the process of the invention, because they provide for the synthesis of cyanoacetates more valuable from an industrial standpoint; methyl chloracetate, ethyl chloracetate, tert-butyl chloracetate.

The alkali metal cyanides reacted in the process according to the invention are preferably sodium cyanide and potassium cyanide.

The alkali metal cyanide is preferably used in amounts such that the molar ratio of the alkali metal cyanide to the chloracetate is greater than or equal to 1, and even more preferably is between 1 and approximately 3.

The hydrocyanic acid, when used, is preferably used in liquid form and in amounts such that the molar ratio of hydrocyanic acid to the chloracetate is greater than 0 and less than or equal to 2. Even more preferably, a ratio of about 1 is used.

The sequestering agent having the Formula (I) is preferably used in amounts such that the molar ratio of the sequestering agent to the chloracetate ranges from about 0.001 to about 0.1. This ratio, even more preferably, ranges from about 0.01 to 0.05.

Preferably, the process according to the invention is carried out at a temperature ranging from about $-30°$ C. to $60°$ C. when no hydrocyanic acid is used, and from $-30°$ C. to $+30°$ C. in the presence of HCN; even more preferably, the subject process is carried out at a temperature ranging from about preferably, $-5°$ C. to about $+20°$ C.

Preferably, an amount of solvent is used such that the number of moles of chloracetate per liter of solvent ranges from about 0.5 to about 5. Even more preferably, the subject process is carried out using about 1 to 3 moles of chloracetate per liter of solvent.

The reaction according to this invention is typically effected at atmospheric pressure, although pressures higher or lower than atmospheric are within the scope of the invention.

The final products according to the invention are compounds having the formula $NC-CH_2-COOR$ wherein R is as above defined, and are particularly useful as pharmaceutical intermediates in the plastics industry.

The sequestering agents of the Formula (I) used in the process according to the invention are conveniently prepared by condensation of a salt of the formula:

$$R_5\text{-}(O-CHR_4-CHR_3)_n-O-M$$

wherein $R_3$, $R_4$, $R_5$ and n are as defined above and M is an alkali metal selected from the group comprising sodium, potassium and lithium, with an amine having the formula:

$$N\text{-}(CHR_1-CHR_2-X)_3$$

wherein $R_1$ and $R_2$ are as above defined and X is chlorine or bromine, or with the corresponding chlorhydrate or bromhydrate.

The molar ratio of the alkali metal salt to the amine ranges from about 3 to about 5.

The condensation is carried out at a temperature between $100°$ and $150°$ C. for 1 to 15 hours in the presence of a solvent which may consist, for example, of chlorobenzene, or preferably an ethylene glycol monoalkylether having the formula:

$$R_5\text{-}(O-CHR_4-CHR_3)_n-OH.$$

The process is preferably carried out such that a solution containing 2 to 5 moles of the alkali metal salt is present per liter of solvent.

The mixture upon completion of the reaction principally comprises the tertiary amine of the formula:

$$N\text{-}[CHR_1\text{---}CHR_2\text{---}O\text{---}(CHR_3\text{---}CHR_4\text{---}O)_n R_5]_3$$

but also contains a small proportion of the corresponding secondary amine:

$$HN\text{-}[CHR_1\text{---}CHR_2\text{---}O\text{---}(CHR_3\text{---}CHR_4\text{---}O)\text{-}{}_n\text{---}R_5]_2$$

and traces of the primary amine:

$$H_2N\text{-}[CHR_1\text{---}CHR_2\text{---}O\text{---}(CHR_3\text{---}CHR_4\text{---}O)_n\text{---}R_5]$$

The tertiary, secondary and primary amines are typically present, after distillation, in the ratio of 90:8:2, respectively.

The mixture obtained as described hereinabove may be directly used in the process according to the invention after the first distillation, i.e., while containing the three different types of amines.

Preferably, however, the reaction mix is more rigorously distilled in order to obtain an essentially pure tertiary amine.

In order to further illustrate the present invention and the advantages thereof, the following specific examples are given, it being understood that same are intended only as illustrative and in nowise limitative.

EXAMPLE 1

Into a thoroughly agitated, double-jacket reactor, equipped with a bulb condenser, 1 liter of anhydrous acetonitrile, cooled to 5° C., was introduced. The following materials were then successively introduced thereto: 56.7 g (2.1 moles) hydrocyanic acid, 171.5 g (1.4 mole) ethylchloracetate and 14.6 g (0.04 mole) tris(3,6-dioxaoctyl)amine.

Following homogenization of the reaction medium, 137.2 g (2.8 moles/1) of dry sodium cyanide were introduced thereto in powder form. The reaction mixture was then vigorously agitated for 8 hours, while maintaining the temperature between 0° and 10° C. Thereafter, the mineral salts were filtered therefrom and then washed twice with 100 ml acetonitrile.

The entire organic solution obtained in this manner was then distilled under reduced pressure. In this manner, 147.1 g ethyl cyanoacetate, representing a yield of 93% with respect to the chloracetate, were obtained, at a rate of conversion of 100%.

EXAMPLES 2 to 11

The procedure of Example 1 was repeated, but under the conditions set forth in Table I for the respective Examples 2 and 11. The results thereof are reported in the Table II which follows.

COMPARATIVE EXAMPLE 1

The procedure of Example 7 was repeated, but without the addition of the sequestering agent. After 8 hours, the degree of conversion was only 5%.

COMPARATIVE EXAMPLE 2

The procedure of Example 11 was repeated, but without the addition of the sequestering agent. After 5 hours, the degree of conversion was only 10%.

EXAMPLE 12

Preparation of Tris(3,6-dioxaheptyl)amine (i) Preparation of sodium 2-methoxyethanolate:

Into a three-necked, one liter flask, equipped with a mechanical agitator, a thermometer and cooling means, 380 g 2-methoxyethanol (5 moles) were introduced. 23 g sodium (1 mole) were then added thereto over the course of 3 hours, while maintaining the temperature of the reaction mixture at 40° C.

(ii) Synthesis of tris(3,6-dioxaheptyl)amine:

To the aforesaid reaction mixture (i), 51.6 g tris(2-chloroethyl)amine chlorhydrate (0.215 moles) were added. The mixture was then heated with reflux of 2-methoxyethanol (125° C.) for 12 hours, followed by the distillation of the solvent under reduced pressure. The excess sodium 2-methoxyethanolate was then neutralized by addition of 11.6 cm$^3$ aqueous HCl (10 N). The sodium chloride was filtered off and the solution distilled.

The tris (3,6-dioxaheptyl)amine distilled between 165° C. and 80° C. under 0.5 mmHg. 49 g of the product were obtained, in a yield of 70%.

The other sequestering agents useful within the scope of this invention are likewise prepared.

TABLE I

| EXAMPLE | Ethyl chloracetate g [mole(s)/liter] | Sodium cyanide g [mole(s)/liter] | HCN g [mole(s)/liter] | Sequestering Agent type (*) g [mole(s)/liter] | Solvent type 1 | Temperature |
|---|---|---|---|---|---|---|
| 2 | 171.5 (1.4) | 98 (2) | 0 | TDA-2 14.6 (0.04) | CH$_3$CN 1 | 50° C. |
| 3 | 171.5 (1.4) | 83.3 (1.7) | 0 | TDA-2 14.6 (0.04) | CH$_3$CN 1 | 50° C. |
| 4 | 171.5 (1.4) | 88.2 (1.8) | 0 | TDA-2 14.6 (0.04) | CH$_3$CN 1 | 0° C. |
| 5 | 85.7 (0.7) | 49 (1) | 0 | TDA-2 7.2 (0.02) | CH$_3$CN 1 | 30° C. |
| 6 | 245 (2) | 98 (2) | 0 | TDA-1 32.5 (0.1) | CH$_3$CN 1 | 20° C. |
| 7 | 245 (2) | 98 (2) | 0 | TDA-1 32.5 (0.1) | CH$_3$CN 1 | 0° C. |

TABLE I-continued

| EXAMPLE | Ethyl chloracetate g [mole(s)/liter] | Sodium cyanide g [mole(s)/liter] | HCN g [mole(s)/liter] | Sequestering Agent type (*) [mole(s)/liter] | Solvent type | Temperature |
|---|---|---|---|---|---|---|
| 8 | 245 (2) | 98 (2) | 0 | TDA-1 32.5 (0.1) | $CH_3CN$ 1 | $-20°$ C. |
| 9 | 171.5 (1.4) | 98 (2) | 54 (2) | TDA-2 14.6 (0.04) | $CH_3CN$ 1 | $0°$ C. |
| 10 | 171.5 (1.4) | 98 (2) | 13.5 (0.5) | TDA-2 14.6 (0.04) | $CH_3CH_2OH$ 1 | $20°$ C. |
| 11 | 343 (2.8) | 166.6 (3.4) | 62.1 (2.3) | TDA-2 29.2 (0.08) | $CH_3CN$ 1 | $20°$ C. |

(*) TDA-1 = tris(3,6-dioxaheptyl)amine
(*) TDA-2 = tris(3,6-dioxaoctyl)amine

TABLE II

| EXAMPLE | Ethyl cyanoacetate obtained | Degree of ethyl chloracetate conversion, in % | Yield with respect to chloracetate used, in % | Reaction time in hour |
|---|---|---|---|---|
| 2 | 114 | 100 | 72 | 1.75 |
| 3 | 118.6 | 100 | 75 | 2 |
| 4 | 115.5 | 100 | 73 | 10 |
| 5 | 55.4 | 100 | 70 | 5 |
| 6 | 162.7 | 100 | 72 | 5 |
| 7 | 169.5 | 100 | 75 | 8 |
| 8 | 101.7 | 60 | 75 | 5 |
| 9 | 150.3 | 100 | 95 | 10 |
| 10 | 137.6 | 100 | 87 | 10 |
| 11 | 297.4 | 100 | 94 | 5 |

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims.

What is claimed is:

1. A process for the preparation of an alkyl cyanoacetate, comprising reacting an alkyl chloracetate having the formula $Cl-CH_2-COOR$, wherein R is lower alkyl, with an excess of an alkali metal cyanide, in an inert solvent and in the presence of at least one tertiary amine sequestering agent having the formula:

$$N + CHR_1 - CHR_2 - O + CHR_3 - CHR_4 - O)_m R_5]_3 \quad (I)$$

wherein $0 \leq n \leq 10$, $R_1$, $R_2$, $R_3$ and $R_4$, which may be the same or different, are each hydrogen or lower alkyl, $R_5$ is alkyl or cycloalkyl having from 1 to 12 carbon atoms, phenyl,

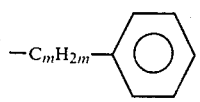

or

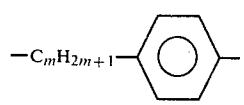

with m ranging from about 1 to 12.

2. The process as defined by claim 1, wherein the sequestering agent (I), $R_1$, $R_2$, $R_3$ and $R_4$, which may be the same or different, are each hydrogen or methyl.

3. The process as defined by claim 1, wherein the sequestering agent (I), $0 \leq n \leq 5$.

4. The process as defined by claim 1, wherein the sequestering agent (I), $R_5$ is alkyl having from 1 to 4 carbon atoms.

5. The process as defined by claim 1, wherein the sequestering agent (I), $R_1$, $R_2$, $R_3$ and $R_4$, which may be the same or different, are each hydrogen or methyl, $0 \leq n \leq 3$, and $R_5$ is alkyl having from 1 to 4 carbon atoms.

6. The process as defined by claim 5, wherein the sequestering agent (I) is tris(3,6-dioxaheptyl)amine having the formula:

$$N + CH_2 - CH_2 - O - CH_2 - CH_2 - O - CH_3)_3.$$

7. The process as defined by claim 5, wherein the sequestering agent (I) is tris(3,6-dioxaoctyl)amine having the formula:

$$N + CH_2 - CH_2 - O - CH_2 - CH_2 - O - C_2H_5)_3.$$

8. The process as defined by claim 1, wherein the molar ratio of the sequestering agent (I) to the alkyl chloracetate ranges from about 0.001 to about 0.1.

9. The process as defined by claim 8, wherein the molar ratio of the sequestering agent (I) to the alkyl chloracetate ranges from about 0.01 to about 0.05.

10. The process as defined by claim 1, wherein the inert solvent is an alcohol or nitrile.

11. The process as defined by claim 10, wherein the inert solvent is selected from the group consisting of methanol, ethanol, the propanols, the butanols, acetonitrile and propionitrile.

12. The process as defined by claim 11, wherein the inert solvent is acetonitrile.

13. The process as defined by claims 1 or 10, wherein the number of moles of alkyl chloracetate per liter of solvent ranges from about 0.5 to about 5.

14. The process as defined by claim 13, wherein the number of moles of alkyl chloracetate per liter of solvent ranges from about 1 to about 3.

15. The process as defined by claim 1, the reaction being conducted in the presence of hydrocyanic acid.

16. The process as defined by claim 15, wherein the molar ratio of the hydrocyanic acid to the alkyl chloracetate is greater than 0 and less than or equal to 2.

17. The process as defined by claim 16, wherein the molar ratio of the hydrocyanic acid to the alkyl chloracetate ranges from about 1 to about 1.5.

18. The process as defined by any of claims 1, 10 or 16, the reaction being carried out at a temperature ranging from about −30° C. to +50° C.

19. The process as defined by claim 18, the reaction being carried out at a temperature ranging from about −5° C. to +20° C.

20. The process as defined by any of claims 1, 10 or 16, the sequestering agent (I) being selected from the group consisting of tris(3-oxaheptyl)amine, tris(3,6-dioxaheptyl)amine, tris(3,6,9-trioxadecyl)amine, tris(3,6-dioxaoctyl)amine, tris(3,6,9-trioxaundecyl)amine, tris(3,6-dioxanonyl)amine, tris(3,6,9-trioxadodecyl)amine, tris(3,6-dioxadecyl)amine, tris(3,6,9-trioxatridecyl)amine, tris(3,6-dioxa-4-methylheptyl)amine, and tris(3,6-dioxa-2,4-dimethylheptyl)amine.

21. The process as defined by any of claims 1, 10 or 16, wherein the alkali metal cyanide is sodium cyanide.

* * * * *